| United States Patent [19] | [11] Patent Number: 4,897,458 |
|---|---|
| Seelmann-Eggebert et al. | [45] Date of Patent: Jan. 30, 1990 |

[54] WATER-SOLUBLE COPOLYMERS AND THEIR PREPARATION

[75] Inventors: Hans-Peter Seelmann-Eggebert, Schriesheim; Dieter Boeckh; Heinrich Hartmann, both of Limburgerhof; Wolfgang Trieselt, Ludwigshafen, all of Fed. Rep. of Germany

[73] Assignee: BASF Aktiengesellschaft, Ludwigshafen, Fed. Rep. of Germany

[21] Appl. No.: 179,049

[22] Filed: Apr. 8, 1988

[30] Foreign Application Priority Data

Apr. 11, 1987 [DE] Fed. Rep. of Germany ....... 3712326
Mar. 4, 1988 [DE] Fed. Rep. of Germany ....... 3807085

[51] Int. Cl.$^4$ .................... C08F 210/02; C08F 30/04
[52] U.S. Cl. .................... 526/318.3; 526/240
[58] Field of Search .................... 526/318.3, 240

[56] References Cited

U.S. PATENT DOCUMENTS

| 2,884,336 | 4/1959 | Loshaek et al. | 526/318.3 |
| 3,137,660 | 6/1964 | Jones | 526/318.3 |
| 3,769,254 | 10/1973 | Anderson et al. | 526/318.3 |
| 4,267,103 | 5/1981 | Cohen | 526/318.3 |

*Primary Examiner*—Joseph L. Schofer
*Assistant Examiner*—N. Sarofim
*Attorney, Agent, or Firm*—William G. Conger

[57] ABSTRACT

Water-soluble copolymers having a K value of from 15 to 120 (determined according to H. Fikentscher in an aqueous solution of their sodium salt at 25° C., a pH of 7 and a polymer concentration of the Na salt of 1% by weight) contain, in polymerized form, (a) not less than 80 mol % of one or more monoethylenically unsaturated $C_3$-$C_6$-monocarboxylic acids,
(b) from 0.5 to 20 mol % of a comonomer which possesses two or more ethylenically unsaturated, non-conjugated double bonds and one or more —CO—OX groups and/or their salt with an alkali metal, ammonium or alkaline earth metal base, and, if required,
(c) not more than 10 mol % of one or more comonomers which differ from (b) and possess two or more ethylenically unsaturated, non-conjugated double bonds, and the said copolymers are prepared by copolymerization of the monomers (a), (b) and, if required (c) in aqueous solution and are used for coating seed.

4 Claims, No Drawings

WATER-SOLUBLE COPOLYMERS AND THEIR PREPARATION

W.O. Application No. 85/01736 discloses that seed can be coated with a polymer mixture which is hygroscopic. The mixture consists of finely divided crosslinked polyacrylamides and finely divided crosslinked polyacrylates. These mixtures may also contain graphite. The seed coated therewith germinates more rapidly than untreated seed. However, the disadvantage is that the high molecular weight, crosslinked polymers are virtually completely non-biodegradable.

It is an object of the present invention to provide substantially biodegradable coating agents for seed.

We have found that this object is achieved, according to the invention, by water-soluble copolymers based on monoethylenically unsaturated carboxylic acids of 3 to 6 carbon atoms if the copolymers have a K value of from 15 to 120 (determined according to H. Fikentscher on the sodium salt in the aqueous solution at 25° C., a pH of 7 and a polymer concentration of the Na salt of 1% by weight) and contain, as copolymerized units, (a) from 99.5 to 80 mol % of one or more monoethylenically unsaturated $C_3$–$C_6$-monocarboxylic acids and (b) from 0.5 to 20 mol % of one or more comonomers which possess two or more ethylenically unsaturated, nonconjugated double bonds and one or more —CO—OX groups in which X is hydrogen, one equivalent of an alkali metal or alkaline earth metal or an ammonium group, with the proviso that the sum of the mol % (a) and (b) is always 100.

The present invention furthermore relates to water-soluble copolymers which have a K value of from 15 to 120 (determined according to H. Fikentscher on the sodium salt in aqueous solution at 25° C., a pH of 7 and a polymer concentration of the Na salt of 1% by weight) and contains, as copolymerized units, (a) not less than 80 mol % of one or more monoethylenically unsaturated $C_3$–$C_6$-monocarboxylic acids, (b) from 0.5 to 20 mol % of one or more comonomers which possess two or more ethylenically unsaturated, non-conjugated double bonds and one or more —CO—OX groups in which X is hydrogen, one equivalent of an alkali metal or alkaline earth metal or an ammonium group and (c) from 0.05 to 10 mol % of one or more comonomers which differ from (b) and possess two or more ethylenically unsaturated, non-conjugated double bonds, with the proviso that the sum of the mol % (a), (b) and (c) is always 100.

The water-soluble copolymers are prepared by copolymerization of a monomer mixture of (a) from 99.5 to 80 mol % of one or more monoethylenically unsaturated $C_3$–$C_6$-monocarboxylic acids and (b) from 0.5 to 20 mol % of one or more comonomers which possess two or more ethylenically unsaturated, non-conjugated double bonds and one or more —CO—OX groups in which X is H, one equivalent of an alkali metal or alkaline earth metal or an ammonium group, in aqueous solution in the presence of a polymerization initiator and, if required, a regulator, the sum of the mol % (a) and (b) always being 100, or by copolymerization of a monomer mixture of (a) not less than 80 mol % of one or more monoethylenically unsaturated $C_3$-$C_6$-monocarboxylic acids, (b) from 0.5 to 20 mol % of one or more comonomers which possess two or more ethylenically unsaturated, non-conjugated double bonds and one or more —CO—OX groups in which X is H, one equivalent of an alkali metal or alkaline earth metal or an ammonium group, and (c) from 0.05 to 10 mol % of one or more comonomers which differ from (b) and possess two or more ethylenically unsaturated, non-conjugated double bonds, in aqueous solution in the presence of a polymerization initiator and a regulator, the sum of the mol % (a), (b) and (c) always being 100.

Suitable components (a) of the water-soluble copolymers are monoethylenically unsaturated $C_3$-$C_6$-monocarboxylic acids. Examples of suitable carboxylic acids of this type are acrylic acid, methacrylic acid, ethacrylic acid, vinylacetic acid, allylacetic acid and crotonic acid. Preferably used monomers of component (a) are acrylic acid and/or methacrylic acid. The monomers of component (a) are present in the copolymer in an amount of from 99.5 to 80, preferably from 97 to 83, mol %.

The monomers of component (b) constitute an important part of the copolymers. These are comonomers which possess two or more ethylenically unsaturated, non-conjugated double bonds and one or more —CO—OH groups and/or their salt with an alkali metal, ammonium or alkaline earth metal base. These comonomers generally increase the molecular weight of the copolymers and are present in the latter in an amount from 0.5 to 20, preferably from 3 to 17, mol %.

The comonomers (b) are obtainable by reacting (b1) maleic anhydride, itaconic anhydride or citraconic anhydride, or a mixture of these, with (b2) polyhydric alcohols of 2 to 6 carbon atoms, water-soluble or water-insoluble polyalkylene glycols having a molecular weight of up to about 400, water-soluble polyalkylene glycols having a molecular weight of from above about 400 to 10,000, polyglycerols having a molecular weight of up to 2,000, polyamines, polyalkylenepolyamines, polyethyleneimines, aminoalcohols, hydroxyamino- or -diaminocarboxylic acids, in particular lysine and serine, water-soluble copolymers of ethylene oxide and carbon dioxide, polyvinyl alcohol having a molecular weight of up to 10,000, allyl alcohol, allylamine, hydroxyalkyl esters, where hydroxyalkyl is of 2 to 6 carbon atoms, of monoethylenically unsaturated $C_3$-$C_6$-carboxylic acids or of saturated $C_3$-$C_6$-hydroxycarboxylic acids or mixtures of these.

Examples of polyhydric alcohols of 2 to 6 carbon atoms are glycol, glycerol, pentaerythritol and monosaccharides, such as glucose, mannose or galactose, uronic acids, such as galacturonic acid, and sugar acids, such as mucic acid or galactonic acid.

Water-soluble polyalkylene glycols are the adducts of ethylene oxide, propylene oxide, n-butylene oxide or isobutylene oxide, or a mixture of these, with polyhydric alcohols of 2 to 6 carbon atoms, for example the adducts of ethylene oxide with glycol, adducts of ethylene oxide with glycerol, adducts of ethylene oxide with pentaerythritol, adducts of ethylene oxide with monosaccharides and the adducts of a mixture of the stated alkylene oxides with polyhydric alcohols. These adducts may be block copolymers of ethylene oxide and propylene oxide, of ethylene oxide and butylene oxides, of ethylene oxide, propylene oxide and butylene oxides. In addition to the block copolymers, adducts which contain the stated alkylene oxides as randomly distributed copolymerized units are also suitable. The molecular weight of the polyalkylene glycols is advantageously up to 5,000, preferably up to 2,000. Preferably used water-soluble polyalkylene glycols are diethylene glycol, triethylene glycol, tetraethylene glycol and polyethylene glycol having a molecular weight of up to 1,500.

Other suitable components (b2) are polyglycerols having a molecular weight of up to 2,000. From this class of substances, diglycerol, triglycerol and tetraglycerol are preferably used.

Preferred polyamines are, for example, diamines, such as ethylenediamine, 1,3-propylenediamine, 1,4-butylenediamine and 1,6-hexamethylenediamine and melamine. Examples of suitable polyalkylenepolyamines are diethylenetriamine, triethylenetetramine, pentaethylenehexamine, N-(3-aminopropyl)-1,3-propanediamine and 3-(2-aminoethyl)aminopropylamine. Particularly suitable polyethyleneimines have a molecular weight of up to 5,000.

Other suitable components (b2)- are aminoalcohols, such as ethanolamine, 2-aminopropan-1-ol, neopentanolamine and 1-methylamino-2-propanol.

Further suitable components (b2) are water-soluble copolymers of ethylene oxide and carbon dioxide, which are obtainable by copolymerization of ethylene oxide and carbon dioxide. Polyvinyl alcohols having a molecular weight of up to 10,000, preferably those having a molecular weight of up to 2,000, are also suitable. The polyvinyl alcohols, which are prepared from polyvinyl acetate by hydrolysis, may be partially or completely hydrolysed. Other suitable compounds of component (b2) are lysine, serine, allyl alcohol, allylamine and hydroxyalkyl esters, where hydroxyalkyl is of 2 to 6 carbon atoms, of monoethylenically unsaturated $C_3$–$C_6$-mono- and dicarboxylic acids.

The hydroxyalkyl ester groups of this group of monomers are derived from polyhydric alcohols, e.g. glycol, glycerol, propane-1,2-diol, propane-1,3-diol, butane-1,4-diol, butane-1,3-diol, butane-2,3-diol, mixtures of butanediols or propanediols, hexane-1,6-diol and neopentylglycol. The polyhydric alcohols are esterified with monoethylenically unsaturated $C_3$–$C_6$-carboxylic acids. These are the carboxylic acids stated above under (a) and (b1). Thus, examples of suitable components (b) are hydroxyethyl acrylate, hydroxyethyl methacrylate, hydroxy-n-propyl methacrylate, hydroxy-n-propyl acrylate, hydroxyisopropyl acrylate, hydroxyisopropyl methacrylate, hydroxy-n-butyl acrylate, hydroxyisobutyl acrylate, hydroxy-n-butyl methacrylate, hydroxyisobutyl methacrylate, hydroxyethyl monomaleate, hydroxyethyl dimaleate, hydroxypropyl monomaleate, hydroxypropyl dimaleate, hydroxy-n-butyl monomaleate, hydroxy-n-dimaleate and hydroxyethyl monoitaconate. Among the hydroxyalkyl esters of the monoethylenically unsaturated dicarboxylic acids, both the monoesters and the diesters of the dicarboxylic acids with the abovementioned polyhydric alcohols are suitable.

Hydroxyalkyl esters of saturated $C_3$–$C_6$-hydroxycarboxylic acids, such as glycol monohydroxyacetate, glycol monolactate and neopentylglcyol hydroxypivalate, are also suitable.

Comonomers (b) obtained from maleic anhydride and ethylene glycol, polyethylene glycol having a molecular weight of up to 2,000, glycerol, diglycerol, triglycerol, tetraglycerol, and polyglycerols having a molecular weight of up to 2,000, pentaerythritol, monosaccharides, neopentylglycol, $\alpha,\omega$-diamines of 2 to 6 carbon atoms, $\alpha, \omega$-diols of 3 to 6 carbon atoms and neopentylglycol monohydroxypivalate are preferably used. Comonomers derived from ethylene glycol and $\alpha,\omega$-diols can be described by, for example, the formula

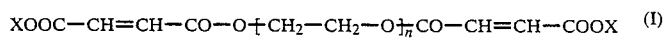

$$XOOC-CH=CH-CO-O+CH_2-CH_2-O+_n CO-CH=CH-COOX \quad (I)$$

where X is H, an alkali metal or an ammonium group and n is from 1 to 120, preferably from 1 to 50.

Comonomers (b) which are formed by reacting maleic anhydride or maleic acid with $\alpha,\omega$-diamines can be defined by the formula

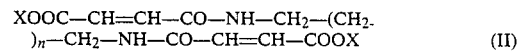

$$XOOC-CH=CH-CO-NH-CH_2-(CH_2-)_n-CH_2-NH-CO-CH=CH-COOX \quad (II)$$

where X is H, an alkali metal or an ammonium group and n is from 0 to 4.

The water-soluble copolymers are prepared by copolymerization of a monomer mixture of (a) from 99.5 to 80 mol % of one or more monoethylenically unsaturated $C_3$–$C_6$-monocarboxylic acids and (b) from 0.5 to 20 mol % of one or more comonomers which possess two or more ethylenically unsaturated, non-conjugated double bonds and one or more —CO—OX groups and/or their salt with an alkali metal, ammonium or alkaline earth metal base, in aqueous solution in the presence of a polymerization initiator.

The sum of the mol % of components (a) and (b) is always 100. The copolymerization is carried out exclusively in an aqueous medium, preferably in a purely aqueous medium. It may be effected by various procedures; for example, the monomers (a) and (b) can be polymerized batchwise in the form of aqueous solutions. It is also possible initially to take some of the monomers and some of the initiators in the polymerization reactor and to heat them to the polymerization temperature under an inert gas atmosphere, and then to add the remaining monomers and the initiator to the reactor at the rate at which the polymerization progresses. The polymerization temperatures are from 20° to 200° C., preferably from 40° to 150° C. At above 100° C., the reaction is carried out in a pressure apparatus.

In a preferred embodiment of the preparation process, the comonomer (b) is first prepared by a method in which (b1) maleic anhydride, itaconic anhydride or citraconic anhydride, or a mixture of these, is initially taken in a reactor and reacted therein, at from 50° to 200° C., with (b2) polyhydric alcohols of 2 to 6 carbon atoms, water-soluble or water-insoluble polyalkylene glycols having a molecular weight of up to about 400, water-soluble polyalkylene glycols having a molecular weight of from above about 400 to 10,000, polyglycerols having a molecular weight of up to 2,000, polyamines, polyalkylenepolyamines, polyethyleneimines, aminoalcohols, hydroxyamino- or -diaminocarboxylic acids, such as lysine and serine, water-soluble copolymers of ethylene oxide and carbon dioxide, polyvinyl alcohol having a molecular weight of up to 10,000, allyl alcohol, allylamine, hydroxyalkyl esters, where hydroxyalkyl is of 2 to 6 carbon atoms, of monoethylenically unsaturated $C_3-C_6$-carboxylic acids or of saturated $C_3-C_6$-hydroxycarboxylic acids or a mixture of these. This reaction is preferably carried out in the absence of water. Instead of the compounds stated under (b1), however, it is also possible to use the mono- or diesters with $C_1-C_4$-alcohols, the said esters being derived from these compounds. In these cases, a transesterification or amidation is carried out, and the resulting $C_1-C_4$-alcohol is preferably distilled off from the reaction mixture. Where amino-containing compounds stated under (b2) are used, the corresponding amides are formed in the reaction with the mono- or diesters of the anhydrides (b1). If esters of component (b1) are used in the preparation of the comonomers (b), these are preferably dimethyl maleate, monomethyl maleate, dimethyl itaconate, monoisopropyl maleate and diisopropyl maleate. Conventional esterification catalysts may also be present.

Not less than 0.5 mole of a compound of component (b1) is used per mole of the compounds (b2). The temperature during the reaction is preferably from 50° to 150° C. The reaction is carried out until conversion of the component (b2) is virtually quantitative. The comonomer (b) may be dissolved in a monoethylenically unsaturated $C_3-C_6$-monocarboxylic acid (a) and then subjected to the copolymerization together with the monomers (a) used as the solvent.

The initially prepared comonomer (b) may, however, also remain in the reaction mixture in which it was prepared and initially may be dissolved therein by adding water or dilute aqueous sodium hydroxide solution. This solution is then copolymerized by adding the comonomers (a). The copolymerization of the monomers (a) and (b) is carried out at a pH of the aqueous solution of from 2 to 9, preferably from 3 to 7. The monomers (a) and (b), each of which contains carboxylic acid groups, can be copolymerized in the form of the free carboxylic acids or in neutralized, preferably partially neutralized, form, the degree of neutralization being from 0 to 100, preferably from 10 to 85, mol %. Neutralization is preferably carried out using alkali metal or ammonium bases. Examples of these are sodium hydroxide solution, potassium hydroxide solution, sodium carbonate, potassium carbonate or ammonium bases, such as ammonia, $C_1-C_{18}$-alkylamines, dialkylamines, such as dimethylamine, di-n-butylamine or dihexylamine, tertiary amines, such as trimethylamine, triethylamine, tributylamine or triethanolamine, and quaternized nitrogen bases, e.g. tetramethylammonium hydroxide, trimethyllaurylammonium hydroxide and trimethylbenzylammonium hydroxide. Neutralization is preferably effected using sodium hydroxide solution, potassium hydroxide solution or ammonia. Neutralization can, however, be carried out using alkaline earth metal bases, e.g. Ca hydroxide or $MgCO_3$.

The water-soluble copolymers may be modified with up to 10 mol % of monomers of group (c). The comonomers (c) used are compounds which possess two or more ethylenically unsaturated double bonds and are not covered by the definition of the compounds (b). Examples of suitable comonomers of group (c) are N,N'-methylenebisacrylamide, polyethylene glycol diacrylates and polyethylene glycol dimethacrylates, each of which is derived from a polyethylene glycol having a molecular weight of from 106 to 4,000, trimethylolpropane triacrylate, trimethylolpropane trimethacrylate, ethylene glycol diacrylate, propylene glycol diacrylate, butanediol diacrylate, hexanediol diacrylate, hexanediol dimethacrylate, diacrylates and dimethacrylates of block copolymers of ethylene oxide and propylene oxide, adducts of ethylene oxide and/or propylene oxide with trimethylolpropane which are diesterified or triesterified with acrylic acid or methacrylic acid, polyhydric alcohols, such as glycerol or pentaerythritol, which are diesterified or polyesterified with acrylic acid or methacrylic acid, triallylamine, tetraallylethylenediamine, divinvylbenzene, diallyl phthalate, polyethylene glycol divinyl ether, trimethylolpropane diallyl ether, polyethylene glycol divinyl ether, butanediol divinyl ether, pentaerythritol triallyl ether and/or divinylethyleneurea. Water-soluble comonomers, e.g. N,N'-methylenebisacrylamide, polyethylene glycol diacrylates, polyethylene glycol dimethacrylates, pentaerythritol triallyl ether and/or divinylurea, are preferably used.

If the comonomers of group (c) are used, they are employed in an amount of from 0.5 to 10, preferably from 0.1 to 6, mol %, based on the monomers present during the polymerization.

The copolymers may contain, as component (d), other water-soluble monoethylenically unsaturated monomers which are copolymerizable with (a), (b) and (c). Examples of suitable monomers of this type are acrylamide, methacrylamide, 2-acrylamido-2-methylpropanesulfonic acid, vinylsulfonic acid, allylsulfonic acid, vinylphosphonic acid, allylphosphonic acid, acrylonitrile, methacrylonitrile, dimethylaminoethyl acrylate, diethylamnoethyl acrylate, diethylaminoethyl methacrylate, N-vinylpyrrolidone, N-vinylformamide, N-vinylimidazole, N-vinylimidazoline, 1-vinyl-2-methyl-2-imidazoline, vinyl acetate and mixtures of the stated monomers. Those monomers of this group which contain acid groups may be used in the copolymerization in the form of the free acid groups or in a form partially or completely neutralized with alkali metal bases or ammonium bases. The basic acrylates, such as diethylaminoethyl acrylate, are neutralized or quaternized with an acid and then subjected to the copolymerization. The monomers (d) are present in the copolymers in an amount of from 0 to 30, preferably from 0 to 20, mol %. They are used merely for modifying the copolymers.

The polymerization initiators used are preferably water-soluble compounds which form free radicals, for example hydrogen peroxide, peroxydisulfates and mixtures of hydrogen peroxide and peroxydisulfates. Examples of suitable peroxydisulfates are lithium peroxydisulfate, sodium peroxydisulfate, potassium peroxydisulfate and ammonium peroxydisulfate. In the case of mixtures of hydrogen peroxide and peroxydisulate, any ratio may be employed; hydrogen peroxide and peroxydisulfate are preferably used in a weight ratio of 3:1 to 1:3. Mixtures of hydrogen peroxide and sodium peroxydisulfate are preferably employed in a weight ratio of 1:1. The abovementioned water-soluble polymerization initiators can, if required, also be used in combination with reducing agents, for example iron(II) sulfate, sodium sulfite, sodium bisulfite, sodium dithionite, triethanolamine and ascorbic acid, in the form of redox initiators. Examples of suitable water-soluble organic peroxides are acetylacetone peroxide, methyl ethyl ketone peroxide, tert-butyl hydroperoxide and cumene hydroperoxide. Furthermore, the water-soluble organic peroxides can be used with the abovementioned reducing agents. Other water-soluble polymerization initiators are azo initiators, e.g. 2,2'-azobis-(2-amidinopropane) dihydrochloride, 2,2'-azobis-(N,N'-dimethylene)-isobutyramidine dihydrochloride, 2-(carbamylazo)-isobutyronitrile and 4,4'-azobis-(4-cyanovaleric acid). The polymerization can also be initiated using water-insoluble initiators, such as dibenzoyl peroxide, dicyclohexyl peroxydicarbonate, dilauryl peroxide or azobisisobutyronitrile.

The initiators are used in the copolymerization of the monomers (a), (b) and, where relevant, (d) in amounts of from 0.1 to 10, preferably from 0.5 to 7, % by weight, based on the sum of the monomers used in the polymerization. The polymerization initiators can be added continuously or batchwise to the mixture to be polymerized, either together with the monomers or separately from these, in the form of aqueous solutions. If the monomers (c) are also used in the copolymerization, the amount of initiator is up to 30, preferably from 5 to 25, % by weight, based on the sum of the monomers used in the polymerization.

The copolymerization may also be carried out in the presence of a regulator. Water-soluble compounds which are either infinitely miscible with water or dissolve therein in an amount of greater than 5% by weight at 20° C. are preferably used for this purpose. Examples of compounds of this type are aldehydes of 1 to 4 carbon atoms, such as formaldehyde, acetaldehyde, propionaldehyde, n-butyraldehyde and isobutyraldehyde, formic acid, ammonium formate, hydroxylammonium salts, in particular hydroxylammonium sulfate, SH-containing compounds of not more than 6 carbon atoms, such as thioglycollic acid, mercapto alcohols, such as mercaptoethanol, mercaptopropanol, mercaptobutanols and mercaptohexanol, monohydric and polyhydric alcohols of not more than 6 carbon atoms, such as isopropanol, glycol, glycerol and isobutanol. Preferred regulators are water-soluble mercaptans, ammonium formate and hydroxylammonium sulfate. The regulators are used in amounts of from 0 to 25% by weight, based on the sum of the monomers used in the polymerization. The particularly effective regulators, which are preferred, are used in amounts of not more than 15% by weight. If the reaction is carried out in the presence of a regulator, the minimum amount used is 0.2% by weight, based on the monomers to be polymerized. If the monomers (c) are used, copolymerization is always carried out in the presence of a regulator.

The preparation of copolymers of
(a) acrylic acid and/or methacrylic acid and
(b) one of the abovementioned comonomers of the formula (I) or (II) or of
(a) acrylic acid and/or methacrylic acid,
(b) one of the abovementioned comonomers of the formula (I) or (II) and
(c) polyethylene glycol diacrylates, polyethylene glycol dimethacrylates and pentaerythritol triallyl ethers is particularly preferred.

In the copolymerization of the monomers (a) and (b) and, where relevant, (c) and (d), aqueous polymer solutions are obtained which have a polymer content of up to 70% by weight. It is of course also possible to prepare very dilute, e.g. 1% strength, aqueous solutions, but for economic reasons the copolymerization is carried out in such a way that aqueous copolymer solutions of not less than 20% strength by weight are prepared. After the copolymerization, the solutions may be brought to a pH of from 6.5 to 7, unless the polymerization was in any case carried out in this range. The copolymers can be obtained by evaporating down the aqueous solutions. They have a low residual monomer content and are surprisingly biodegradable. The biodegradability of the novel copolymers is up to 100%, according to DIN 38,412, Part 24, Static Test (L25), and is as a rule from 20 to 95%. The K value of the copolymers (determined according to H. Fikentscher) is preferably from 20 to 80.

The copolymers are water-soluble. If they are insoluble in water in the form of the free acid, they can be converted to a water-soluble form by partial or complete neutralization with NaOH, KOH, ammonia or amines. Copolymers or their alkali metal or ammonium salts which have a solubility of not less than 20 g per liter of water at 20° C. are regarded as water-soluble in the present context. The copolymers surprisingly have the advantage that, at low polymer concentrations, they do not exhibit precipitation in aqueous solutions containing Ca and/or Mg ions. It is therefore possible to prepare stable solutions of the copolymers in tap water without the alkaline earth metal salts of the copolymers being precipitated.

The copolymers are used as coating agents for seed. In seed coating, where all cereal species, such as wheat, rye, oats and barley, as well as corn and lupins and other seed can be coated with a polymer film, more rapid germination of the seed is achieved compared with the uncoated seed. From 0.1 to 1 kg of the copolymers is used per 100 kg of seed. The copolymers are preferably sprayed onto the seed in the form of a dilute aqueous solution and form a protective polymer film on the seed. Finely divided, inert fillers, e.g. graphite, quartz, talc or bentonite, having a particle size of from 20 to 500 μm may be incorporated in the polymer film. The fillers are preferably applied together with the polymer solution to the material to be coated.

The K values stated in the Examples were determined according to H. Fikentscher, Cellulosechemie, 13 (1932), 58–64 and 71–74; $K = k \times 10^3$. The measurements were carried out on the sodium salt in aqueous solution at 25° C., a pH of 7 and a polymer concentration of the Na salt of 1% by weight. If novel copolymers are obtained in the form of other salts or of the free acids, they must first be converted to the sodium salts before the K value is determined. The molecular weights stated in the Examples refer to the number average molecular weight. The data on biodegradability were determined according to DIN 38,412, Part 24, Static Test (L25).

EXAMPLE 1

In a 2 l glass reactor equipped with a stirrer, a thermometer, a nitrogen inlet and 3 feed vessels, 98 g (1 mole) of maleic anhydride and 0.1 g of p-toluenesulfonic acid are initially taken and are heated together with the amounts, stated in Table 1, of a polyhydric alcohol under the conditions likewise stated in Table 1, and with stirring, until esterification is complete. The melt is cooled in each case to 20° C., after which 200 ml of water and, where relevant, the amounts of regulator stated in Table 1 are added and the aqueous solution is heated to 80° C. in the course of 20 minutes while nitrogen is passed through.

The polymerization is then carried out as follows: the particular ethylenically unsaturated carboxylic acids stated in Table 1 and an equimolar amount of 25% strength aqueous sodium hydroxide solution are added dropwise over a period of 4 hours and, beginning at the same time as the monomer addition, the initiator, dissolved in 100 ml of water is added dropwise over a period of 5 hours from the third feed vessel. During the addition of the monomers and initiator, the reaction mixture is stirred under a nitrogen atmosphere. The polymerization is carried out at 80° C. When the addition of the initiator is complete, the reaction mixture is polymerized for a further hour at 80° C., cooled to 20° C. and then brought to pH 6.5 with 25% strength aqueous sodium hydroxide solution. The properties of the resulting copolymers are stated in Table 1.

The biodegradability of the copolymers was additionally demonstrated by bacterial growth experiments. For this purpose, a concentration medium was prepared on slid nutrient substrates and solidified with 18 g/l of agar. The concentration medium had the following composition:

| | |
|---|---|
| disodium hydrogen phosphate dihydrate | 7 g/l |
| potassium dihydrogen phosphate | 3 g/l |
| sodium chloride | 0.5 g/l |
| ammonium chloride | 1.0 g/l |
| solution of trace elements | 2.5 ml/l pH 7.0 |

(prepared according to T. Bauchop and S. R. Elsden, J. gen. Mikrobiol. 23 (1960), 457–469).

The copolymers described in Table 1 under nos. 1, 4, 7 and 11 were added to the nutrient media in each case in a concentration of 10 g/l.

Soil samples were either introduced into a liquid medium and shaken there for 7 days at 30° C. or introduced in the form of an aqueous suspension directly onto solid nutrient substrates and likewise incubated at 30° C. The concentration cultures in the liquid medium were transferred to solid nutrient substrates after 7 days. Fast growing colonies were removed from these plates and tested for uniformity in a thin smear.

Pure bacteria cultures which showed clear growth on the copolymers tested were isolated in this manner.

When the bacterial growth experiments described above were carried out, for comparison, using a copolymer of 30% by weight of maleic acid and 70% by weight of acrylic acid, having a K value of 60, there was no detectable bacterial growth.

TABLE 1

| | Esterification with ... mole of polyhydric alcohols | | Copolymerization | | | | | | | | Copolymer | | |
|---|---|---|---|---|---|---|---|---|---|---|---|---|---|
| | | | At [°C.] | Time [h] | Monomer (a) | | Comonomer (b) | | ...% by wt. of initiator, based on (a) + (b) | | ...% by wt. of regulator, based on (a) + (b) | K value | Residual monomer content [% by wt.] | Biodegradability [%] |
| No. | | | | | [moles] | [mol %] | [moles] | [mol %] | | | | | | |
| 1 | 0.5 | ethylene glycol | 70 | 1 | 4AS | 88.9 | 0.5 | 11.1 | H₂O₂ | 5 | — | 43.7 | 0.18 | 61 |
| 2 | 0.5 | butanediol | 70 | 1 | 4AS | 88.9 | 0.5 | 11.1 | H₂O₂ | 5 | — | 45.4 | 0.21 | 63 |
| 3 | 0.5 | neopentylglycol | 70 | 1.5 | 4AS | 88.9 | 0.5 | 11.1 | H₂O₂ | 5 | — | 38.2 | 0.15 | 72 |
| 4 | 0.5 | PEG₄₀₀ | 80 | 2.5 | 4AS | 88.9 | 0.5 | 11.1 | H₂O₂ | 5 | — | 17.3 | 0.28 | 91 |
| 5 | 0.5 | HPN | 80 | 2.5 | 4AS | 85.7 | 0.5 | 11.1 | H₂O₂ | 5 | — | 37.8 | 0.21 | 66 |
| 6 | 0.5 | neopentylglycol | 70 | 1.5 | 3AS | 88.9 | 0.5 | 14.3 | H₂O₂ / Na₂S₂O₈ | 5 / 1 | — | 15.8 | 0.23 | 78 |
| 7 | 0.33 | glycerol | 90 | 4.5 | 4AS | 92.4 | 0.33 | 7.6 | H₂O₂ / Na₂S₂O₈ | 5 / 1 | — | 19.2 | 0.19 | 82 |
| 8 | 0.5 | neopentylglycol | 70 | 1.5 | 5AS | 90.9 | 0.5 | 9.1 | H₂O₂ / Na₂S₂O₈ | 5 / 1 | mercaptoethanol 1 | 32.4 | 0.23 | 62 |
| 9 | 0.5 | neopentylglycol | 70 | 1.5 | 5MAS | 90.9 | 0.5 | 9.1 | H₂O₂ / Na₂S₂O₈ | 5 / 1 | — | 29.8 | 0.19 | 58 |
| 10 | 0.5 | ethylene glycol | 70 | 1 | 5MAS | 90.9 | 0.5 | 9.1 | H₂O₂ / Na₂S₂O₈ | 5 / 1 | — | 24.2 | 0.17 | 71 |
| 11 | 0.25 | pentaerythritol | 100 | 3 | 5AS | 95.2 | 0.25 | 4.8 | H₂O₂ / Na₂S₂O₈ | 5 / 1 | hydroxylammonium sulfate 1 | 32.1 | 0.24 | 63 |

AS acrylic acid; MAS methacrylic acid

For the copolymers stated under nos. 1 and 4 in Table 1, the precipitation behavior was tested at pH 7.5 in aqueous solutions which contained from 10 to 10,000 mg/l of Ca ions (in the form of CaCl₂). The following Ca ion concentrations were tested: 10, 50, 75, 100, 150, 500, 1,000 and 10,000 mg/l. The copolymer concentrations were varied from 0.1 to 7 mg/l (the following concentrations were tested: 0.1, 0.5, 1.0, 2, 3, 4 and 7 mg of copolymer per l of water). No precipitation occurred even after the aqueous solutions of the copolymers were stored for 20 days in the presence of Ca ions, whereas a copolymer of 30% by weight of maleic acid and 70% by weight of acrylic acid, having a K value of 60, always gave precipitates under the stated test conditions.

EXAMPLE 2

Preparation of the comonomer (b) of the formula

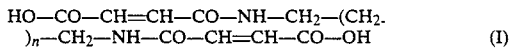

$$HO-CO-CH=CH-CO-NH-CH_2-(CH_2-)_n-CH_2-NH-CO-CH=CH-CO-OH \qquad (I)$$

Comonomer Ia: n=0 in formula I

A solution of 1.5 moles (147 g) of maleic anhydride in 350 g of dimethylformamide is initially taken in a 1 l glass reactor equipped with a stirrer, condenser and a feed vessel. A solution of 0.75 mole of ethylenediamine in 150 g of dimethylformamide is added to this solution at 40° C. over a period of 1.5 hours. The reaction is carried out at from 40° to 60° C. The resulting suspension is stirred at 60° C. for a further hour at the end of the addition of the ethylenediamine. The suspension is then evaporated down by distilling off dimethylformamide under reduced pressure, and the remaining residue is filtered off. The filter cake is boiled up briefly with acetone. Thereafter, the solids are filtered off and dried. The comonomer of the abovementioned formula I, where n is 0, is obtained in a yield of 91%. Preparation of comonomer (Ib): n=4 in formula I The procedure described for the preparation of comonomer (Ia) is followed, except that 0.75 mole of 1,6-hexamethylenediamine is used instead of ethylenediamine. This procedure gives the comonomer (Ib) in a yield of 89%. Copolymerization In a 2 l glass reactor equipped with a stirrer, a thermometer, a nitrogen inlet, a condenser and two feed vessels, 0.5 mole of the comonomer Ia, 300 ml of water and 2% by weight, based on comonomer Ia, of acrylic acid are initially taken and are heated to 90° C. while stirring and while nitrogen is passed through. For the copolymerization, 1,075 g of 35% strength aqueous sodium acrylate solution (4 moles of sodium acrylate) are then added over a period of 5 hours, and 33 g of 2,2'-azobis-(2-amidinopropane) dihydrochloride, dissolved in 170 ml of water, are added over a period of 6 hours. The copolymerization is carried out at 90° C. and while passing through nitrogen. A viscous yellowish brown solution is obtained, which is further polymerized at 90° C. for 1 hour after the end of the addition of the initiator and then cooled to 30° C. and brought to pH 6 with 25% strength aqueous sodium hydroxide solution. The composition of the monomer mixture during the copolymerization is 88.9 mol % of acrylic acid and 11.1 mol % of comonomer Ia. The resulting copolymer has a K value of 36.2 and a residual monomer content of acrylic acid of 0.1% by weight. The biodegradability is 36%.

The copolymerization of the comonomer Ib is carried out in the same manner as described above for the comonomer Ia. In this case too, a monomer mixture of 88.9 mol % of acrylic acid and 11.1 mol % of comonomer Ib is subjected to the copolymerization. This gives a copolymer having a K value of 38.7 and a residual monomer content of 0.22% of acrylic acid. The biodegradability is 41%.

EXAMPLE 3

In a 2 l glass reactor equipped with a stirrer, a thermometer and three feed vessels, one of which is heatable and stirrable, 500 ml of water are initially taken and heated to 90° C. At the same time, 98 g (1 mole) of maleic anhydride are heated to 80° C. in the heatable feed vessel, and 0.5 mole of serine is added a little at a time over a period of 3 hours. After the addition of the serine, the reaction mixture is stirred in the heatable dropping funnel for a further hour at 80° C. The reaction of the maleic anhydride with serine to form the comonomer (b) is then complete.

The copolymerization of the monomer (b) is then carried out as follows: 1,075 g of a 35% strength sodium acrylate solution (4 moles of sodium acrylate) and the melt of comonomer (b) are added dropwise under a stream of nitrogen over a period of 5 hours to the initially taken mixture heated at 90° C. and, beginning at the same time, 90 g of 30% strength hydrogen peroxide, dissolved in 60 ml of water, are added dropwise under a stream of nitrogen to the said mixture over a period of 6 hours. In this way, a monomer mixture of 88.9 mol % of sodium acrylate and 11.1 mol % of crosslinking agent (b) (reaction product of maleic anhydride and serine) is subjected to the copolymerization. In the course of the copolymerization, a viscous solution is formed, which is heated at 95° C. for a further hour after the end of the addition of the initiator, after which the said solution is cooled and brought to pH 6.5 by adding 25% strength aqueous sodium hydroxide solution. The resulting polymer has a K value of 43.6 and a residual monomer content of acrylic acid of 0.13% by weight. The biodegradability is 43%.

EXAMPLE 4

Example 3 is repeated except that, instead of serine, 0.5 mole of lysine is used for the preparation of the comonomer. Copolymerization of the monomer mixture consisting of 88.9 mol % of sodium acrylate and 11.1 mol % of the comonomer (b) of maleic anhydride and lysine give a copolymer having a K value of 39.2 and a residual monomer content of 0.19% by weight. The biodegradability is 36%.

EXAMPLES 5 TO 9

In a 4 l glass reactor equipped with a stirrer, a thermometer, a nitrogen inlet and six feed vessels, 800 ml of water are initially taken and heated to 90° C. while flushing with nitrogen. During this time, the feed vessels are charged as stated below:
Feed I: solution of p moles of the comonomers stated in the Table, in 2 moles of acrylic acid
Feed II: 2 moles of acrylic acid
Feed III: solution of m % by weight of a regulator in 100 ml of water
Feed IV: solution of n moles of the dimaleate stated in the Table below, in 300 ml of water
Feed V: 640 g of 25% strength aqueous sodium hydroxide solution
Feed VI: 25 g of sodium persulfate dissolved in 500 ml of 30% strength $H_2O_2$.

At 90° C., and beginning at the same time, the feeds I and III are metered in over a period of 2 hours, feed IV in the course of 4 hours and feed VI over a period of 5½ hours. Two hours after the beginning of the monomer addition, feed II is added dropwise over a period of 2 hours and feed V over a period of 3 hours.

Thereafter, the mixture is allowed to react for a further hour, cooled and then brought to pH 7 with 25% strength sodium hydroxide solution.

The amounts of comonomers (b) and (c) used in the Examples, the amounts of acrylic acid (comonomer (a)) and the regulators used (% by weight) and the K values of the resulting polymers are listed in Table 2.

TABLE 2

| Example No. | Comonomer (a) [moles]; [mol %] | Comonomer (b) m[moles]; [mol %] | Comonomer (c) n[moles]; [mol %] | Regulator m[% by wt.] | K value |
| --- | --- | --- | --- | --- | --- |
| 5 | acrylic acid 4; 87.9 | ethylene glycol dimaleate 0.45; 9.9 | ethylene glycol diacrylate 0.10; 2.2 | mercapto-ethanol 5 | 36.1 |
| 6 | acrylic acid 4; 86.0 | diethylene glycol dimaleate | $PEG_{400}$ diacrylate | mercapto-ethanol | 32.3 |

TABLE 2-continued

| Example No. | Comonomer (a) [moles]; [mol %] | Comonomer (b) m[moles]; [mol %] | Comonomer (c) n[moles]; [mol %] | Regulator m[% by wt.] | K value |
|---|---|---|---|---|---|
| 7 | acrylic acid 4; 85.1 | 0.60; 12.9 ethylene glycol dimaleate | 0.05; 1.1 triethylene glycol diacrylate | 8 mercapto- ethanol | 34.1 |
| 8 | acrylic acid 4; 82.5 | 0.50; 10.6 PEG$_{400}$ dimaleate | 0.20; 4.3 tetraethylene glycol diacrylate | 7 mercapto- ethanol | 28.7 |
| 9 | acrylic acid 4; 83.3 | 0.70; 14.4 triethylene glycol dimaleate 0.55; 11.5 | 0.15; 3.1 glycerol diacrylate 0.25; 5.2 | 10 mercapto- ethanol 11 | 28.3 |

PEG$_X$ polyethylene glycol of a mean molecular weight of X

The biodegradability of the copolymers was demonstrated by bacterial growth experiments. For this purpose, a concentration medium was prepared on solid nutrient substrates and solidified with 18 g/l of agar. The concentration medium had the following composition:

| | |
|---|---|
| disodium hydrogen phosphate dihydrate | 7 g/l |
| potassium dihydrogen phosphate | 3 g/l |
| sodium chloride | 0.5 g/l |
| ammonium chloride | 1.0 g/l |
| solution of trace elements | 2.5 ml/l pH 7.0 |

(prepared according to T. Bauchop and S. R. Elsden, J. gen. Mikrobiol. 23 (1960), 457-469).

The copolymers described in the Table were each added to the nutrient media in a concentration of 10 g/l.

Soil samples were either introduced into a liquid medium and shaken there for 7 days at 30° C. or introduced in the form of an aqueous suspension directly onto solid nutrient substrates and likewise incubated at 30° C. The concentration cultures in the liquid medium were transferred to solid nutrient substrates after 7 days. Fast growing colonies were removed from these plates and tested for uniformity in a thin smear.

Pure bacteria cultures which showed clear growth on the copolymers tested were isolated in this manner.

When the bacterial growth experiments described above were carried out, for comparison, using a copolymer of 30% by weight of maleic acid and 70% by weight of acrylic acid, having a K value of 60, there was no detectable bacterial growth.

We claim:

1. A water-soluble copolymer based on monoethylenically unsaturated carboxylic acids of 3 to 6 carbon atoms, wherein the copolymer has a K value of from 15 to 120 (determined on the sodium salt according to H. Fikentscher in aqueous solution at 25° C., a pH of 7 and a polymer concentration of the Na salt of 1% by weight) and contains, as copolymerized units,
   (a) from 99.5 to 80 mol % of one or more monoethylenically unsaturated C$_3$-C$_6$-monocarboxylic acids and
   (b) from 0.5 to 20 mol % of one or more comonomers which possess two or more ethylenically unsaturated, non-conjugated double bonds and one or more —CO—OX groups in which X is hydrogen, one equivalent of an alkali metal or alkaline earth metal or an ammonium group,
with the proviso that the sum of the mol % (a) and (b) is always 100.

2. A water-soluble copolymer as claimed in claim 1, wherein
   (a) not less than 80 mol % of one or more monoethylenically unsaturated C$_3$-C$_6$-monocarboxylic acids,
   (b) from 0.5 to 20 mol % of one or more comonomers which possess two or more ethylenically unsaturated, non-conjugated double bonds and one or more —CO—OX groups in which X is hydrogen, one equivalent of an alkali metal or alkaline earth metal or an ammonium group, and
   (c) from 0.05 to 10 mol % of one or more comonomers which differ from (b) and possess two or more ethylenically unsaturated, non-conjugated double bonds, with the proviso that the sum of the mol % (a), (b) and (c) is always 100.

3. A water-soluble copolymer as claimed in claim 2, which contains, as copolymerizable units,
   (a) acrylic acid, methacrylic acid, or a mixture of both,
   (b) a compound of the formula

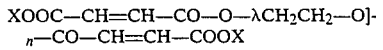

where X is H, an alkali metal, or an ammonium group and n is from 1 to 120, and
   (c) polyethylene glycol diacrylates, polyethylene glycol dimethacrylates, or pentaerythitol triallylether.

4. A water-soluble copolymer as claimed in claim 1, which contains, as copolymerizable units,
   (a) acrylic acid, methacrylic acid, or a mixture of both, and
   (b) a compound of the formula

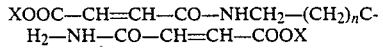

where X is H, an alkali metal or an ammonium group and n is from 0 to 4.

* * * * *

UNITED STATES PATENT AND TRADEMARK OFFICE
CERTIFICATE OF CORRECTION

PATENT NO. : 4,897,458

DATED : January 30, 1990

INVENTOR(S) : Hans-Peter Seelmann-Eggebert Et Al

It is certified that error appears in the above-identified patent and that said Letters Patent is hereby corrected as shown below:

Column 14, line 42 should read as follows:
$XOOC-CH=CH-CO-O-[CH_2CH_2-O]-$

Signed and Sealed this

Twelfth Day of May, 1992

Attest:

DOUGLAS B. COMER

Attesting Officer

Acting Commissioner of Patents and Trademarks